(12) United States Patent
Henry

(10) Patent No.: US 11,484,499 B2
(45) Date of Patent: Nov. 1, 2022

(54) PHARMACEUTICAL FORMULATIONS OF PEGYLATED LIPOSOMES AND BLOOD COAGULATION FACTORS

(71) Applicant: Cantab Biopharmaceuticals Patents Limited, Valletta (MT)

(72) Inventor: William Henry, London (GB)

(73) Assignee: Cantab Biopharmaceuticals Patents Limited, Valeria (MT)

( * ) Notice: Subject to any disclaimer, the term of this patent is extended or adjusted under 35 U.S.C. 154(b) by 0 days.

(21) Appl. No.: 16/052,300

(22) Filed: Aug. 1, 2018

(65) Prior Publication Data

US 2019/0060235 A1     Feb. 28, 2019

Related U.S. Application Data

(63) Continuation of application No. 15/517,148, filed as application No. PCT/EP2015/073003 on Apr. 5, 2017, now abandoned.

(30) Foreign Application Priority Data

Oct. 6, 2014   (GB) ...................................... 1417589

(51) Int. Cl.
  *A61K 9/127*   (2006.01)
  *A61K 38/36*   (2006.01)
  (Continued)

(52) U.S. Cl.
  CPC .......... *A61K 9/1271* (2013.01); *A61K 9/0019* (2013.01); *A61K 9/1278* (2013.01);
  (Continued)

(58) Field of Classification Search
  CPC ................................................... A61K 9/1271
  See application file for complete search history.

(56) References Cited

U.S. PATENT DOCUMENTS

| 5,013,556 A | 5/1991 | Woodle et al. |
| 5,925,739 A * | 7/1999 | Spira ...................... A61K 38/37 |
| | | 424/94.3 |

(Continued)

FOREIGN PATENT DOCUMENTS

| CN | 1774281 A | 5/2006 |
| JP | 2003-531862 A | 10/2003 |

(Continued)

OTHER PUBLICATIONS

AM Hvas, HT Sorensen, L Norengaard, K Christiansen, J Ingerslev, B Sorensen. "Tranexamic acid combined with recombinant factor VIII increases clot resistance to accelerated fibrinolysis in severe hemophilia A." Journal of Thrombosis and Haemostasis, vol. 5, 2007, pp. 2408-2414. (Year: 2007).*

(Continued)

*Primary Examiner* — Isaac Shomer
(74) *Attorney, Agent, or Firm* — Wilmer Cutler Pickering Hale and Dorr LLP

(57) ABSTRACT

The present invention provides a pharmaceutical composition for subcutaneous administration comprising a blood factor and a colloidal particle comprising about 0.5 to 20 mole percent of an amphipathic lipid derivatized with a biocompatible hydrophilic polymer, wherein the blood factor is not encapsulated in said colloidal particle.

13 Claims, 2 Drawing Sheets

Specification includes a Sequence Listing.

```
ATRRYYLGAVELSWDYMQSDLGELPVDARFPPRVPKSFPFNTSVVYKKTLFVEFTDHLFN
IAKPRPPWMGLLGPTIQAEVYDTVVITLKNMASHPVSLHAVGVSYWKASEGAEYDDQTSQ
REKEDDKVFPGGSHTYVWQVLKENGPMASDPLCLTYSYLSHVDLVKDLNSGLIGALLVCR
EGSLAKEKTQTLHKFILLFAVFDEGKSWHSETKNSLMQDRDAASARAWPKMHTVNGYVNR
SLPGLIGCHRKSVYWHVIGMGTTPEVHSIFLEGHTFLVRNHRQASLEISPITFLTAQTLL
MDLGQFLLFCHISSHQHDGMEAYVKVDSCPEEPQLRMKNNEEAEDYDDDLTDSEMDVVRF
DDDNSPSFIQIRSVAKKHPKTWVHYIAAEEEDWDYAPLVLAPDDRSYKSQYLNNGPQRIG
RKYKKVRFMAYTDETFKTREAIQHESGILGPLLYGEVGDTLLIIFKNQASRPYNIYPHGI
TDVRPLYSRRLPKGVKHLKDFPILPGEIFKYKWTVTVEDGPTKSDPRCLTRYYSSFVNME
RDLASGLIGPLLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLSVFFSGYTFKH
KMVYEDTLTLFPFSGETVFMSMENPGLWILGCHNSDFRNRGMTALLKVSSCDKNTGDYYE
DSYEDISAYLLSKNNAIEPRSFSQNPPVLKRHQREITRTTLQSDQEEIDYDDTISVEMKK
EDFDIYDEDENQSPRSFQKKTRHYFIAAVERLWDYGMSSSPHVLRNRAQSGSVPQFKKVV
FQEFTDGSFTQPLYRGELNEHLGLLGPYIRAEVEDNIMVTFRNQASRPYSFYSSLISYEE
DQRQGAEPRKNFVKPNETKTYFWKVQHHMAPTKDEFDCKAWAYFSDVDLEKDVHSGLIGP
LLVCHTNTLNPAHGRQVTVQEFALFFTIFDETKSWYFTENMERNCRAPCNIQMEDPTFKE
NYRFHAINGYIMDTLPGLVMAQDQRIRWYLLSMGSNENIHSIHFSGHVFTVRKKEEYKMA
LYNLYPGVFETVEMLPSKAGIWRVECLIGEHLHAGMSTLFLVYSNKCQTPLGMASGHIRD
FQITASGQYGQWAPKLARLHYSGSINAWSTKEPFSWIKVDLLAPMIIHGIKTQGARQKFS
SLYISQFIIMYSLDGKKWQTYRGNSTGTLMVFFGNVDSSGIKHNIFNPPIIARYIRLHPT
HYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLF
FQNGKVKVFQGNQDSFTPVVNSLDPPLLTRYLRIHPQSWVHQIALRMEVLGCEAQDLY
```

(51) Int. Cl.
A61K 38/37 (2006.01)
A61K 9/00 (2006.01)
A61K 38/48 (2006.01)

(52) U.S. Cl.
CPC ............ A61K 38/36 (2013.01); A61K 38/37 (2013.01); A61K 38/4833 (2013.01); A61K 38/4846 (2013.01); A61K 38/4866 (2013.01)

(56) References Cited

U.S. PATENT DOCUMENTS

| | | | | |
|---|---|---|---|---|
| 6,156,337 | A * | 12/2000 | Barenholz | A61K 9/1277 264/4.1 |
| 6,586,001 | B1 * | 7/2003 | Zalipsky | A61K 9/1272 424/1.21 |
| 2002/0115590 | A1 * | 8/2002 | Johannessen | A61K 38/4846 514/14.3 |
| 2003/0134778 | A1 * | 7/2003 | Baru | A61K 9/1272 514/1.1 |
| 2003/0232075 | A1 | 12/2003 | Nelsestuen | |
| 2007/0141135 | A1 | 6/2007 | Balu-Iyer et al. | |
| 2007/0167359 | A1 | 7/2007 | Baru et al. | |
| 2009/0117087 | A1 | 5/2009 | Carroll et al. | |
| 2019/0060235 | A1 * | 2/2019 | Henry | A61P 17/02 |

FOREIGN PATENT DOCUMENTS

| | | | |
|---|---|---|---|
| JP | 2010-514819 A | 5/2010 | |
| WO | WO-95/04524 A1 | 2/1995 | |
| WO | WO-99/55306 A1 | 11/1999 | |
| WO | WO-01/05873 A1 | 1/2001 | |
| WO | WO-2004/091723 A1 | 10/2004 | |
| WO | WO-2007/002886 A2 | 1/2007 | |
| WO | WO-2010/140061 A2 | 12/2010 | |
| WO | WO-2011/022707 A1 | 2/2011 | |
| WO | WO-2011/135307 A1 | 11/2011 | |
| WO | WO-2011/135308 A1 | 11/2011 | |
| WO | WO-2012031018 A1 * | 3/2012 | ........... A61K 31/435 |
| WO | WO-2013/156488 A2 | 10/2013 | |

OTHER PUBLICATIONS

JV Jokerst, T Lobovkina, RN Zare, SS Gambhir. "Nanoparticle PEGylation for imaging and therapy." Nanomedicine, vol. 6(4), 2011, pp. 715-728. (Year: 2011).*

J Pan et al. "Enhanced efficacy of recombinant FVIII in noncovalent complex with PEGylated liposome in hemophilia A in mice." Blood, vol. 114 No. 13, Sep. 2009, pp. 2802-2811. (Year: 2009).*

V. S. Blanchette. "Prophylaxis in the haemophilia population." Haemophilia (2010), 16 (Suppl. 5), pp. 181-188. (Year: 2010).*

Marilyn J. Manco-Johnson et al. "Prophylaxis versus Episodic Treatment to Prevent Joint Disease in Boys with Severe Hemophilia." The New England Journal of Medicine, vol. 357, No. 6, Aug. 9, 2007, pp. 535-544. (Year: 2007).*

Hemophilia NewsToday. https://hemophilianewstoday.com/hemophilia-treatments/prophylaxis/ accessed Aug. 13, 2021, pp. 1-5. (Year: 2021).*

Oliver Michel Theusinger, Johannes Nurnberg, Lars M. Asmis, Burkhardt Seifert, Donat Rudolf Spahn. "Rotation thromboelastometry (ROTEM) stability and reproducibility over time." European Journal of Cardio-thoracic Surgery 37 (2010), pp. 677-683. (Year: 2010).*

Baru et al., Factor VIII efficient and specific non-covalent binding to PEGylated liposomes enables prolongation of its circulation time and haemostatic efficacy, Thrombosis & Haemostasis, vol. 93, No. 6, pp. 1061-1068, May 11, 2005.

International Search Report and Written Opinion dated Dec. 14, 2015, in the International Application No. PCT/EP2015/073003, filed on Oct. 6, 2015, 12 pages.

Peng et al., "PEGylation of a Factor VIII-Phosphatidylinositol Complex: Pharmacokinetics and Immunogenicity in Hemophilia A Mice," The AAPS Journal, vol. 14, No. 1, pp. 35-42, Mar. 2012.

Spira et al., "Prolonged bleeding-free period following prophylactic infusion of recombinant factor VIII reconstituted with pegylated liposomes", Blood, vol. 108, No. 12, pp. 3668-3673, Dec. 1, 2006.

United States Court of Appeals for the Federal Circuit, "*Intendis GmbH* v. *Glenmark Pharmaceuticals*," Case 2015-1902, Decided May 16, 2016, pp. 1-17, (Year: 2016).

Pan et al., "Enhanced efficacy of recombinant FVIII in noncovalent complex with PEGylated liposome in hemophilia A mice," Blood, Sep. 24, 2009, vol. 114, No. 13, pp. 2802-2811.

Ramani et al., "Passive Transfer of Polyethylene glycol to Liposomal-Recombinant Human FVIII Enhances its Efficacy in a Murine Model for Hemophilia A," Journal of Pharmaceutical Sciences, Sep. 2008, vol. 97, No. 9, pp. 3753-3764.

International Search Report and Written Opinion dated Dec. 22, 2016, in the International Application No. PCT/EP2016/074759, filed Oct. 14, 2016, 12 pages.

Lichtenberg et al., "Liposomes: Preparation, Characterization, and Preservation," Methods of Biochemical Analysis, Mar. 16, 1988, vol. 33, pp. 337-462.

Peng et al., "PEGylation of a Factor VIII-Phosphatidylinositol Complex: Pharmacokinetics and Immunogenicity in Hemophilia A Mice" The AAPS Journal, Mar. 2012, vol. 14, Issue 1, pp. 35-42, first publlished online: Dec. 16, 2011.

Spira et al., "Prolonged bleeding-free period following prophylactic infusion of recombinant factor VIII reconstituted with pegylated liposomes," Blood, published online Aug. 3, 2006, vol. 108, pp. 3668-3673.

Yatuv et al., "Binding of proteins to PEGylated liposomes and improvement of G-CSF efficacy in mobilization of hematopoietic stem cells", Journal of Controlled Release, Apr. 2, 2009, vol. 135, Issue 2, pp. 44-50.

Palchetti et al., "The protein corona of circulating PEGylated liposomes," Biochimica et Biophysica Acta, Feb. 2016, vol. 1858, pp. 189-196.

Yatuv et al., "The use of PEGylated liposomes in the development of drug delivery applications for the treatment of hemophilia," International Journal of Nanomedicine, Aug. 5, 2010, vol. 5, pp. 581-591.

* cited by examiner

```
ATRRYYLGAVELSWDYMQSDLGELPVDARFPPRVPKSFPFNTSVVYKKTLFVEFTDHLFN
IAKPRPPWMGLLGPTIQAEVYDTVVITLKNMASHPVSLHAVGVSYWKASEGAEYDDQTSQ
REKEDDKVFPGGSHTYVWQVLKENGPMASDPLCLTYSYLSHVDLVKDLNSGLIGALLVCR
EGSLAKEKTQTLHKFILLFAVFDEGKSWHSETKNSLMQDRDAASARAWPKMHTVNGYVNR
SLPGLIGCHRKSVYWHVIGMGTTPEVHSIFLEGHTFLVRNHRQASLEISPITFLTAQTLL
MDLGQFLLFCHISSHQHDGMEAYVKVDSCPEEPQLRMKNNEEAEDYDDDLTDSEMDVVRF
DDDNSPSFIQIRSVAKKHPKTWVHYIAAEEEDWDYAPLVLAPDDRSYKSQYLNNGPQRIG
RKYKKVRFMAYTDETFKTREAIQHESGILGPLLYGEVGDTLLIIFKNQASRPYNIYPHGI
TDVRPLYSRRLPKGVKHLKDFPILPGEIFKYKWTVTVEDGPTKSDPRCLTRYYSSFVNME
RDLASGLIGPLLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLSVFFSGYTFKH
KMVYEDTLTLFPFSGETVFMSMENPGLWILGCHNSDFRNRGMTALLKVSSCDKNTGDYYE
DSYEDISAYLLSKNNAIEPRSFSQNPPVLKRHQREITRTTLQSDQEEIDYDDTISVEMKK
EDFDIYDEDENQSPRSFQKKTRHYFIAAVERLWDYGMSSSPHVLRNRAQSGSVPQFKKVV
FQEFTDGSFTQPLYRGELNEHLGLLGPYIRAEVEDNIMVTFRNQASRPYSFYSSLISYEE
DQRQGAEPRKNFVKPNETKTYFWKVQHHMAPTKDEFDCKAWAYFSDVDLEKDVHSGLIGP
LLVCHTNTLNPAHGRQVTVQEFALFFTIFDETKSWYFTENMERNCRAPCNIQMEDPTFKE
NYRFHAINGYIMDTLPGLVMAQDQRIRWYLLSMGSNENIHSIHFSGHVFTVRKKEEYKMA
LYNLYPGVFETVEMLPSKAGIWRVECLIGEHLHAGMSTLFLVYSNKCQTPLGMASGHIRD
FQITASGQYGQWAPKLARLHYSGSINAWSTKEPFSWIKVDLLAPMIIHGIKTQGARQKFS
SLYISQFIIMYSLDGKKWQTYRGNSTGTLMVFFGNVDSSGIKHNIFNPPIIARYIRLHPT
HYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLF
FQNGKVKVFQGNQDSFTPVVNSLDPPLLTRYLRIHPQSWVHQIALRMEVLGCEAQDLY
```

Fig. 1

SYSDGDQCASSPCQNGGSCKDQLQSYICFCLPAFEGRNCETHKDDQLICVNENGGCEQYCSDHTGTKR
SCRCHEGYSLLADGVSCTPTVEYPCGKIPILEKRNASKPQGR

Fig. 2

KPVAFSDYIHPVCLPDR

Fig. 3

GHQFEGAEEYASFLQEAQVPFLSLERCSAPDVHGSSILPGMLCAGFLEGGTDACQGDSGGPLVCEDQA
AERRLTLQGIISWGSGCGDRNKPGVYTDVAYYLAWIREHTVS

Fig. 4

PHARMACEUTICAL FORMULATIONS OF PEGYLATED LIPOSOMES AND BLOOD COAGULATION FACTORS

CROSS-REFERENCES TO RELATED APPLICATIONS

This application is a continuation of U.S. patent application Ser. No. 15/517,148 filed on Apr. 5, 2017, which claims priority to National Stage Entry of PCT/EP2015/073003 filed on Oct. 6, 2015 which claims priority to GB1417589.7 filed Oct. 6, 2014, the entire contents of which are incorporated herein.

SEQUENCE LISTING

The instant application contains a Sequence Listing which has been submitted electronically in ASCII format and is hereby incorporated by reference in its entirety. Said ASCII copy, created on Oct. 6, 2014, is named 123 US1 Sequence Listing.txt and is 15070 bytes in size.

The present invention relates to pharmaceutical compositions of blood factors for subcutaneous administration.

Typically, blood factors have been prepared as pharmaceutical compositions for intravenous administration. The compositions have been based on the active protein, often conjugated to a polymer such as polyethylene glycol (PEG) to improve the half-life in circulation. Intravenous administration of PEGylated blood factors as therapeutic agents is therefore well understood and widely accepted. Liposomal formulations of naked (i.e. unconjugated and without modification) blood factors such as Factor VIII and Factor IX substances are known also, see for example WO 95/04524.

Pharmaceutical compositions comprising Factor VIII and liposomes modified by the presence of polyethylene glycol are described in WO 99/55306 in which the blood factor is not encapsulated in the liposome. However, the formulations are prepared for intravenous administration. Additional formulations of other proteins are described in WO 2004/091723 where the proteins include blood clotting factors. The proteins are said to bind to the liposomes in a non-covalent manner through interaction with the polyethylene glycol present on the surface of the liposomes. However, the formulations of blood clotting factors prepared according to the examples of this document are also for intravenous administration.

Other examples of formulations of blood factors, Factor VIII and Factor VIIa, present as a conjugate with PEG are shown in WO 2011/135307 and WO 2011/135308 respectively where the actual formulations prepared were for intravenous administration. WO 2013/156488 also describes a dosage form of modified therapeutic agents, including blood factors such as Factor VIII (FVIII) and Factor VIIa (FVIIa), for subcutaneous administration.

Factor VIII has also been found to be capable of association with PEGylated liposomes, i.e. the blood factor is not encapsulated inside the liposome (Baru et al Thromb. Haemost., 93, pages 1061-1068, (2005)). However, the compositions of FVIII were only prepared as formulations for intravenous administration.

Further studies by Peng et al in *The AAPS Journal*, 14(1), pages 25-42 (2011) disclose an alternative approach based on FVIII encapsulated in liposomes which are subsequently PEGylated by passively adding PEG to the liposomes after preparation. In one experiment in Peng et al the liposomal formulation is administered subcutaneously (SC) to investigate immunogenicity but there is no suggestion of a therapeutic purpose to this administration. In Peng et al there is also a specific reference to the paper of Baru et al (2005) and a statement that the approach of Baru et al "exposed FVIII to plasma components such as proteases and IgGs". Liposomes prepared according to the method of Baru et al (2005) containing recombinant Factor VIII have been administered intravenously to subjects (Spira et al *Blood*, 108 (12), pages 3668-3673 (2012)).

Current methodologies for formulating blood factors for administration rely on intravenous modes of administration. This is problematic since the patient inevitably receives a large bolus injection of the active agent at several time points leading an uneven therapeutic level of agent in the blood of the patient.

There is therefore a need for pharmaceutical composition of a blood factor which can provide a safe and effective dosage.

According to the present invention there is provided a pharmaceutical composition for subcutaneous administration comprising a blood factor and a colloidal particle comprising approximately 0.5 to 20 mole percent of an amphipathic lipid derivatized with a biocompatible hydrophilic polymer, wherein the blood factor is not encapsulated in said colloidal particle.

The colloidal particles may be substantially neutral and the polymer may carry substantially no net charge. The colloidal particles may have a mean particle diameter of between about 0.03 to about 0.4 microns ($\mu$m), for example having a mean particle diameter of approximately 0.1 microns ($\mu$m). A mean particle diameter in this range may increase the circulation time of the particles in vivo and prevent their adsorption by the reticuloendothelial system (RES).

The blood factor may be selected from the group consisting of Factor VIII, Factor VIIa, Factor VII, Factor IX, Factor X, Factor Xa, Factor XI, Factor V, Factor XII, Factor XIII, von Willebrand's Factor (vWF), prothrombin, or Protein C and/or a fragment thereof. The blood factor may be used in a lyophilised form when preparing the pharmaceutical composition.

BRIEF DESCIRPTION OF THE DRAWINGS

FIG. 1 shows a B-domain truncated Factor VIII sequence.
FIG. 2 shows a Factor VII fragment sequence.
FIG. 3 shows a thrombin B-chain fragment sequence.
FIG. 4 shows a Factor XII fragment sequence.

Where the composition comprises a fragment of a blood factor, the factor may suitably be an active fragment thereof in which the fragment retains the biological activity, or substantially the same biological activity as the native blood factor. For example, one such active fragment is the B-domain truncated Factor VIII sequence shown in FIG. 1. Other fragments include, the Factor VII fragment shown in FIG. 2, the thrombin B-chain fragment shown in FIG. 3, the Factor XII fragment shown in FIG. 4, and the D'D3 domains of vWF.

It is further possible that the composition may comprise both the native blood factor and a fragment thereof.

The pharmaceutical composition of the invention may also additionally comprise another therapeutically active compound or molecule, e.g. an anti-inflammatory drug, analgesic or antibiotic, or other pharmaceutically active agent which may promote or enhance the activity of Factor VIIa, Factor VII, Factor VIII, Factor IX, Factor X, Factor Xa, Factor XI, Factor V, Factor XIII, von Willebrand's Factor (vWF), prothrombin or Protein C, or a fragment thereof, such as for example another blood coagulation factor.

The terms Factor VIIa (FVIIa) and Factor VII (FVII) are also used interchangeably unless the context specifies otherwise. FVIII is used as an abbreviation for Factor VIII, FIX is used as an abbreviation for Factor IX, and so on for all the blood factors described herein mutatis mutandis.

The blood coagulation (clotting) factor may be from any suitable source and may be a recombinant protein produced by recombinant DNA technology using molecular biological techniques or synthesised chemically or produced transgenically in the milk of a mammal, or the factor may be isolated from natural sources (e.g. purified from blood plasma). Suitably the factor is a mammalian blood clotting factor, such as a human blood clotting factor. References to a blood clotting factor include a blood coagulation factor.

As discussed above, blood factors are all characterised inter alia by the property of surface adhesion. This is a necessary feature of the coagulation cascade which requires that enzymes and cofactors adhere to other participants in the cascade, to the surface of platelets and to tissue at the site of injury. Indeed it is particularly important that a blood clot remains at the site of injury and does not drift to cause a dangerous thrombosis. This property presents a challenge in the formulation of drug products, since blood factors such as VIIa, VIII and IX will adhere excessively to any glass and plastic surfaces. In practical terms this is mitigated by the extensive use of polysorbate (e.g. Tween® 80).

The colloidal particles of the invention are typically in the form of lipid vesicles or liposomes as are well known in the art. References to colloidal particles in the present specification include liposomes and lipid vesicles unless the context specifies otherwise.

In the colloidal particles, the amphipathic lipid may be a phospholipid from natural or synthetic sources. The amphipathic lipid may comprise approximately 0.5 to about 20 mole percent (%) of the particles, for example approximately about 1 to 20%, or about 1 to 6%, or about 3%.

Suitable examples of such amphipathic lipids include phosphatidylethanolamine (PE), a carbamate-linked uncharged lipopolymer or aminopropanediol distearoyl (DS), or mixtures thereof. A suitable example of phosphatidyl ethanolamine (PE) may be 1,2-distearoyl-sn-glycero-3-phosphoethanol-(DSPE). The purpose of the biocompatible hydrophilic polymer is to sterically stabilize the SUVs, thus preventing fusion of the vesicles in vitro, and allowing the vesicles to escape adsorption by the RES in vivo.

The colloidal particles may further comprise a second amphipathic lipid obtained from either natural or synthetic sources. The second amphipathic lipid may be phosphatidylcholine (PC). A suitable example of phosphatidyl choline (PC) may be palmitoyl-oleoyl phosphatidyl choline (POPC).

In such an embodiment, the pharmaceutical composition may be composed of colloidal particles which comprise palmitoyl-oleoyl phosphatidyl choline (POPC) and 1,2-distearoyl-sn-glycero-3-phosphoethanol-amine (DSPE) in a ratio (POPC:DSPE) of from 85 to 99:15 to 1. In some cases, the ratio of POPC:DSPE may be from 90 to 99:10 to 1. In one embodiment, the ratio of POPC:DSPE may be 97:3.

In an alternative embodiment, the pharmaceutical composition of the invention may be supplemented with cholesterol.

The biocompatible polymer may have a molecular weight of between about 500 to about 5000 Daltons, for example approximately 2000 Daltons.

The biocompatible hydrophilic polymer used according to the invention may be selected from the group consisting of polyalkylethers, polylactic acids and polyglycolic acids. The biocompatible hydrophilic polymer may be polyethylene glycol (PEG). The polyethylene glycol as used in the compositions of the invention may have a molecular weight of between about 500 to about 5000 Daltons, for example it may have a molecular weight of approximately 1000, 2000, or 3000 Daltons. In one embodiment the molecule weight of the PEG may be 2000 Daltons. The polyethylene glycol may be branched or unbranched.

An example of a suitable derivatized amphipathic lipid may be 1,2-distearoyl-sn-glycero-3-phosphoethanol-amine-N-[poly-(ethyleneglycol)]. If the PEG has a molecular weight of 2000 Daltons, the derivatized amphipathic lipid may be described as 1,2-distearoyl-sn-glycero-3-phosphoethanol-amine-N-[poly-(ethyleneglycol)-2000] (DSPE-PEG 2000).

The pharmaceutical composition may comprise any suitable excipient, buffer and/or adjuvant. Examples of such excipient, buffer and/or adjuvants, include phosphate buffered saline (PBS), potassium phosphate, sodium phosphate and/or sodium citrate. Other biological buffers can include PIPES, MOPS etc.

Suitable pH values for the pharmaceutical composition include any generally acceptable pH values for administration in vivo, such as for example pH 5.0 to pH 9.0, suitably from pH 6.8 to pH 7.2, or pH 7.0.

The present inventors have surprisingly found that formulations of blood factors in association with colloidal particles (liposomes) derivatized with a biocompatible polymer can be successfully administered subcutaneously and achieve a therapeutically effective dose of blood factor to a subject suffering from haemophilia. Suitably, the biocompatible polymer is polyethylene glycol.

In the examples of the present invention the PEG is incorporated into the liposome during vesicle formation, before association with the blood factor. It is believed that specific amino acid sequences on the blood factor may bind non-covalently to carbamate functions of the PEG molecules on the outside of the liposomes.

Although there is a reference in Peng et al (2011) to the administration of the liposomal FVIII to mice subcutaneously (SQ) it is quite clear that this was only done to look at relative immunogenicity and was not considered as a viable treatment option. To highlight this, the authors clearly state at the top of page 41 that "FVIII-PI/PEG was given intravenously, the clinical route of administration for FVIII." In other words, Peng et al does not disclose or even suggest subcutaneous administration as a viable treatment option. Further, the authors in Peng et al (2011) also state on page 40 that their approach is "distinctively different" to that of Baru et al (2005). The most recent publications in the field therefore present mutually exclusive and different alternatives to the present invention.

As discussed above, the liposome does not encapsulate the blood factor(s) so that smaller sized liposomes may be used if desired which have a longer half-life in vivo, since they are not removed by the reticuloendothelial system (RES). The activity of the formulated blood factors is not impaired as shown in the Examples with full activity found in vitro and immediately after injection in vivo.

The blood factors interact non-covalently with the polymer chains on the external surface of the liposomes, and no chemical reaction is carried out to activate the polymer chains, unlike the composition disclosed in EP-A-0689428. The nature of the interaction between the blood factor and the liposome derivatized with a biocompatible hydrophilic polymer may be by any non-covalent mechanism, such as ionic interactions, hydrophobic interactions, hydrogen bonds and Van der Waals attractions (Arakawa, T. and Timasheff, S. N., *Biochemistry* 24: 6756-6762 (1985); Lee, J. C. and Lee, L. L. Y., *J. Biol. Chem.* 226: 625-631 (1981)). An example of such a polymer is polyethylene glycol (PEG).

A variety of known coupling reactions may be used for preparing vesicle forming lipids derivatized with hydrophilic polymers. For example, a polymer (such as PEG) may be derivatized to a lipid such as phosphatidylethanolamine (PE) through a cyanuric chloride group. Alternatively, a capped PEG may be activated with a carbonyl diimidazole coupling reagent, to form an activated imidazole compound. A carbamate-linked compound may be prepared by reacting the terminal hydroxyl of MPEG (methoxyPEG) with p-nitrophenyl chloroformate to yield a p-nitrophenyl carbonate. This product is then reacted with 1-amino-2,3-propanediol to yield the intermediate carbamate. The hydroxyl groups of the diol are acylated to yield the final product. A similar synthesis, using glycerol in place of 1-amino-2,3-propanediol, can be used to produce a carbonate-linked product, as described in WO 01/05873. Other reactions are well known and are described, e.g. in U.S. Pat. No. 5,013,556.

Colloidal particles (liposomes) can be classified according to various parameters. For example, when the size and number of lamellae (structural parameters) are used as the parameters then three major types of liposomes can be described: Multilamellar vesicles (MLV), small unilamellar vesicles (SUV) and large unilamellar vesicles (LW).

MLV are the species which form spontaneously on hydration of dried phospholipids above their gel to liquid crystalline phase transition temperature ($T_m$). The size of the MLVs is heterogeneous and their structure resembles an onion skin of alternating, concentric aqueous and lipid layers.

SUV are formed from MLV by sonication or other methods such as extrusion, high pressure homogenisation or high shear mixing and are single layered. They are the smallest species with a high surface-to-volume ratio and hence have the lowest capture volume of aqueous space to weight of lipid.

The third type of liposome LUV has a large aqueous compartment and a single (unilamellar) or only a few (oligolamellar) lipid layers. Further details are disclosed in D. Lichtenberg and Y. Barenholz, in "*Liposomes: Preparation, Characterization, and Preservation, in Methods of Biochemical Analysis*", Vol. 33, pp. 337-462 (1988).

As used herein the term "loading" means any kind of interaction of the biopolymeric substances to be loaded, for example, an interaction such as encapsulation, adhesion (to the inner or outer wall of the vesicle) or embedding in the wall with or without extrusion of the biopolymeric substances.

As used herein and indicated above, the term "liposome" refers to colloidal particles and is intended to include all spheres or vesicles of any amphipathic compounds which may spontaneously or non-spontaneously vesiculate, for example phospholipids where at least one acyl group replaced by a complex phosphoric acid ester. The liposomes may be present in any physical state from the glassy state to liquid crystal. Most triacylglycerides are suitable and the most common phospholipids suitable for use in the present invention are the lecithins (also referred to as phosphatidylcholines (PC)), which are mixtures of the diglycerides of stearic, palmitic, and oleic acids linked to the choline ester of phosphoric acid. The lecithins are found in all animals and plants such as eggs, soybeans, and animal tissues (brain, heart, and the like) and can also be produced synthetically. The source of the phospholipid or its method of synthesis are not critical, any naturally occurring or synthetic phosphatide can be used.

Examples of specific phosphatides are L-a-(distearoyl) lecithin, L-a-(dipalmitoyl) lecithin, L-a-phosphatide acid, L-a-(dilauroyl)-phosphatidic acid, L-a(dimyristoyl) phosphatidic acid, L-a(dioleoyl)phosphatidic acid, DL-a (dipalmitoyl) phosphatidic acid, L-a(distearoyl) phosphatidic acid, and the various types of L-a-phosphatidylcholines prepared from brain, liver, egg yolk, heart, soybean and the like, or synthetically, and salts thereof. Other suitable modifications include the controlled peroxidation of the fatty acyl residue cross-linkers in the phosphatidylcholines (PC) and the zwitterionic amphipathates which form micelles by themselves or when mixed with the PCs such as alkyl analogues of PC.

The phospholipids can vary in purity and can also be hydrogenated either fully or partially. Hydrogenation reduces the level of unwanted peroxidation, and modifies and controls the gel to liquid/crystalline phase transition temperature ($T_m$) which effects packing and leakage.

The liposomes can be "tailored" to the requirements of any specific reservoir including various biological fluids, maintains their stability without aggregation or chromatographic separation, and remains well dispersed and suspended in the injected fluid. The fluidity in situ changes due to the composition, temperature, salinity, bivalent ions and presence of proteins. The liposome can be used with or without any other solvent or surfactant.

Generally suitable lipids may have an acyl chain composition which is characteristic, at least with respect to transition temperature ($T_m$) of the acyl chain components in egg or soybean PC, i.e., one chain saturated and one unsaturated or both being unsaturated. However, the possibility of using two saturated chains is not excluded.

The liposomes may contain other lipid components, as long as these do not induce instability and/or aggregation and/or chromatographic separation. This can be determined by routine experimentation.

The biocompatible hydrophilic polymer may be physically attached to the surface of the liposome, or inserted into the membrane of the liposome. The polymer may therefore be covalently bound to the liposome.

A variety of methods for producing the modified liposomes which are unilamellar or multilamellar are known and available (see Lichtenberg and Barenholz, (1988)):

1. A thin film of the phospholipid is hydrated with an aqueous medium followed by mechanical shaking and/or ultrasonic irradiation and/or extrusion through a suitable filter;
2. Dissolution of the phospholipid in a suitable organic solvent, mixing with an aqueous medium followed by removal of the solvent;
3. Use of gas above its critical point (i.e., freons and other gases such as $CO_2$ or mixtures of $CO_2$ and other gaseous hydrocarbons) or
4. Preparing lipid detergent mixed micelles then lowering the concentration of the detergents to a level below its critical concentration at which liposomes are formed.

In general, such methods produce liposomes with heterogeneous sizes from about 0.02 to 10 µm or greater. Since liposomes which are relatively small and well defined in size are preferred for use in the present invention, a second processing step defined as "liposome down-sizing" can be used for reducing the size and size heterogeneity of liposome suspensions.

The liposome suspension may be sized to achieve a selective size distribution of vesicles in a size range less than about 5 µm, for example <0.4 µm. In one embodiment of the invention, the colloidal particles have an average particle size diameter of from about 0.03 to 0.4 microns (µm), suitably around 0.1 microns (µm).

Liposomes in this range can readily be sterilized by filtration through a suitable filter. Smaller vesicles also show less of a tendency to aggregate on storage, thus reducing potentially serious blockage or plugging problems when the liposome is injected intravenously or subcutaneously. Finally, liposomes which have been sized down to the submicron range show more uniform distribution.

Several techniques are available for reducing the sizes and size heterogeneity of liposomes, in a manner suitable for the present invention. Ultrasonic irradiation of a liposome suspension either by standard bath or probe sonication produces a progressive size reduction down to small unilamellar vesicles (SUVs) between 0.02 and 0.08 µm in size.

Homogenization is another method which relies on shearing energy to fragment large liposomes into smaller ones. In a typical homogenization procedure the liposome suspension is recirculated through a standard emulsion homogenizer until selected liposome sizes, typically between about 0.1 and 0.5 µm are observed. In both methods, the particle size distribution can be monitored by conventional laser-beam particle size determination.

Extrusion of liposomes through a small-pore polycarbonate filter or equivalent membrane is also an effective method for reducing liposome sizes down to a relatively well-defined size distribution whose average is in the range between about 0.02 and 5 µm, depending on the pore size of the membrane.

Typically, the suspension is cycled through one or two stacked membranes several times until the desired liposome size distribution is achieved. The liposome may be extruded through successively smaller pore membranes to achieve a gradual reduction in liposome size.

Centrifugation and molecular sieve chromatography are other methods which are available for producing a liposome suspension with particle sizes below a selected threshold less than 1 µm. These two respective methods involve preferential removal of large liposomes, rather than conversion of large particles to smaller ones. Liposome yields are correspondingly reduced.

The size-processed liposome suspension may be readily sterilized by passage through a sterilizing membrane having a particle discrimination size of about 0.4 µm, such as a conventional 0.45 µm depth membrane filter. The liposomes are stable in lyophilized form and can be reconstituted shortly before use by taking up in water.

Suitable lipids for forming liposomes are described above. Suitable examples include but are not limited to phospholipids such as dimirystoylphosphatidylcholine (DMPC) and/or dimirystoyl-phosphatidylglycerol (DMPG), egg and soybean derived phospholipids as obtained after partial or complete purification, directly or followed by partial or complete hydrogenation.

The following four methods are described in WO 95/04524 and are generally suitable for the preparation of the colloidal particles (liposomes) used in accordance with the present invention.

Method A a) mixing amphipathic substances, such as lipids suitable for forming vesicles in water-immiscible organic solvents b) removing of the solvent in presence of a solid support, alternatively, dried amphipathic substances or mixtures thereof can be used in any form (powder, granular, etc.) directly, c) taking up the product of step b) into a solution of the biopolymeric substances in a physiologically compatible solution d) adding an organic solvent having solubilizing or dispersing properties, as well as e) drying the fraction obtained in step d) under conditions retaining the function of the biopolymeric substances.

According to step a) of Method A amphipathic substances suitable for forming vesicles as mentioned above are mixed in a water-immiscible organic solvent. The water-immiscible organic solvent may be a polar-protic solvent such as fluorinated hydrocarbons, chlorinated hydrocarbons and the like.

In step b) of the method of the invention the solvent is removed in presence of a solid support. The solid support may be an inert organic or inorganic material having a bead-like structure. The material of the inorganic support material may be glass and the organic material can be Teflon™ or other similar polymers.

The step c) of Method A of the invention is for taking up the product of step b) into a solution of the substances to be encapsulated in a physiologically compatible solution.

The physiological compatible solution may be equivalent to a sodium chloride solution up to about 1.5 by weight. It is also possible to use other salts as long as they are physiologically compatible e.g. as a cryoprotectant e.g., sugars and/or amino acids. For example, lactose, sucrose or trehalose may be used as a cryoprotectant.

Optionally, between step a) and b) a step of virus inactivation, sterilizing, depyrogenating, filtering the fraction or the like of step a) can be provided. This might be advantageous in order to have a pharmaceutically acceptable solution at an early stage of the preparation.

The step d) of the Method A is adding an organic solvent having solubilizing or dispersing properties.

The organic solvent may be an organic polar-protic solvent miscible with water. Lower aliphatic alcohols having 1 to 5 carbon atoms in the alkyl chain can also be used, such as tertiary butanol (tert-butanol). The amount of organic polar-protic solvent miscible with water is strongly dependent on its interference with the substance to be loaded to the liposomes. For example, if a protein is to be loaded the upper limit is set by the amount of solvent by which the activity of the protein becomes affected. This may strongly vary with the nature of the substance to be loaded. For example, if the blood clotting factor comprises Factor IX then the amount of about of tert-butanol is around 30%, whereas, for Factor VIII an amount of less than 10% of tert-butanol is suitable (Factor VIII is much more sensitive to the impact of tert-butanol). The percentage of tert-butand in these examples is based on percent by volume calculated for final concentration.

Optionally, subsequent to step d), virus inactivation sterilizing and/or portioning of the fraction yielded after step d) can be carried out.

The step e) of the present invention is drying the fraction obtained in step d) under conditions retaining the function of the substance to be loaded. One method for drying the mixture is lyophilization. The lyophilization may be carried out in presence of a cryoprotectant, for example, lactose or other saccharides or amino acids. Alternatively, evaporation or spray-drying can be used.

The dried residue can then be taken up in an aqueous medium prior to use. After taking up of the solid it forms a dispersion of the respective liposomes. The aqueous medium may contain a saline solution and the dispersion formed can optionally be passed through a suitable filter in order to down size the liposomes if necessary. Suitably, the liposomes may have a size of 0.02 to 5 µm, for example in the range of <0.4 µm.

The liposomes obtainable by the Method A show high loading of the blood factors.

The pharmaceutical compositions of the invention can also be an intermediate product obtainable by isolation of either fraction of step c) or d) of the method A. Accordingly, the formulation of the invention also comprises an aqueous dispersion obtainable after taking up the product of step e) of method A in water in form of a dispersion (liposomes in aqueous medium).

Alternatively, the pharmaceutical compositions of the invention are also obtainable by the following methods which are referred to as Methods B, C, D and E.

Method B

This method comprises also the steps a), b) and c) of the Method A. However, step d) and e) of Method A are omitted.

Method C

In Method C step d) of method A is replaced by a freeze and thaw cycle which has to be repeated at least two times. This step is well-known in prior art to produce liposomes.

Method D

Method D excludes the use of any osmotic component. In method D the steps of preparation of vesicles, admixing and substantially salt free solution of the substances to be loaded and co-drying of the fractions thus obtained is involved.

Method E

Method E is simpler than methods A-D described above. It requires dissolving the compounds used for liposome preparation (lipids antioxidants, etc.) in a polar-protic water miscible solvent such as tert-butanol. This solution is then mixed with an aqueous solution or dispersion containing the blood factor. The mixing is performed at the optimum volume ratio required to maintain the biological and pharmacological activity of the agent.

The mixture is then lyophilized in the presence or absence of cryoprotectant. Rehydration is required before the use of the liposomal formulation. These liposomes are multilamellar, their downsizing can be achieved by one of the methods described in WO 95/04524.

The invention also includes methods of treatment of a blood clotting disease (e.g. haemophilia) or trauma in a subject comprising administering subcutaneously a pharmaceutical composition or dosage as defined herein to a subject in need thereof. Such methods may include, a method of treatment of a blood clotting disease or trauma in a subject wherein the patient has developed antibodies (i.e. inhibitors) to a blood factor.

Blood clotting diseases or disorders may be characterised by a loss of function of a blood clotting factor, or the generation of auto-antibodies. Examples of blood clotting diseases include haemophilia, such as haemophilia A and haemophilia B.

The present invention therefore extends to a pharmaceutical composition as defined above for use in the treatment of a blood clotting disease (e.g. haemophilia) or trauma. Such pharmaceutical compositions for use the treatment of a blood clotting disease or trauma may be used where the patient has developed antibodies to said blood factor. Uses of the invention in accordance with this aspect also include the use of a blood factor in the manufacture of a medicament as defined above for use in the treatment of a blood clotting disease or trauma.

Factor VIIa can be used in the treatment of bleeding episodes in haemophilia A or B, or in treatment of patients who have developed inhibitory antibodies against FVIII or IX, respectively. Factor VIII can be used in the treatment of bleeding episodes in patients with haemophilia A and Factor IX can be used in the treatment of patients with haemophilia B.

As used herein, the term "treatment" includes any regime that can benefit a human or a non-human mammal. The treatment of "non-human mammals" extends to the treatment of domestic mammals, including horses and companion animals (e.g. cats and dogs) and farm/agricultural animals including members of the ovine, caprine, porcine, bovine and equine families. The treatment may be in respect of any existing condition or disorder, or may be prophylactic (preventive treatment). The treatment may be of an inherited or an acquired disease. The treatment may be of an acute or chronic condition.

Levels of activity in the blood coagulation cascade may be measured by any suitable assay, for example the Whole Blood Clotting Time (WBCT) test or the Activated Partial Thromboplastin Time (APTT).

The Whole Blood Clotting Time (WBCT) test measures the time taken for whole blood to form a clot in an external environment, usually a glass tube or dish.

The Activated Partial Thromboplastin Time (APTT) test measures a parameter of part of the blood clotting pathway. It is abnormally elevated in haemophilia and by intravenous heparin therapy. The APTT requires a few millilitres of blood from a vein. The APTT time is a measure of one part of the clotting system known as the "intrinsic pathway". The APTT value is the time in seconds for a specific clotting process to occur in the laboratory test. This result is always compared to a "control" sample of normal blood. If the test sample takes longer than the control sample, it indicates decreased clotting function in the intrinsic pathway. General medical therapy usually aims for a range of APTT of the order of 45 to 70 seconds, but the value may also be expressed as a ratio of test to normal, for example 1.5 times normal. A high APTT in the absence of heparin treatment can be due to haemophilia, which may require further testing.

The invention also provides a kit of parts comprising a pharmaceutical composition of the invention, and an administration vehicle including an injectable solution for subcutaneous administration, said kit suitably comprising instructions for use thereof.

The invention therefore may also suitable provide a dosage form of a pharmaceutical composition of the invention. Such dosage forms may be provided as suitable containers or vials containing the appropriate dose for a patient.

The pharmaceutical compositions for subcutaneous administration or dosage forms of the invention may be administered alone or in conjunction with other compounds, such as therapeutic compounds or molecules, e.g. anti-inflammatory drugs, analgesics or antibiotics, or other pharmaceutically active agents which may promote or enhance the activity of Factor VIIa, Factor VII, Factor VIII, Factor IX, Factor X, Factor Xa, Factor XI, Factor V, Factor XIII, von Willebrand's Factor (vWF), prothrombin or Protein C, or a fragment thereof, such as for example another blood coagulation factor. Such administration with other compounds may be simultaneous, separate or sequential. The components may be prepared in the form of a kit which may comprise instructions as appropriate.

The pharmaceutical compositions of the invention allow for improved treatment of diseases where a blood factor is administered to treat a patient suffering from of a blood clotting disease or trauma.

In one embodiment of the invention there is provided a pharmaceutical composition for subcutaneous administration comprising a blood factor and a colloidal particle comprising approximately 1-20 mole percent of an amphipathic lipid derivatized with a biocompatible hydrophilic polymer, a pharmaceutically acceptable buffer, adjusted to physiological pH suitable for subcutaneous administration, wherein the blood factor is not encapsulated in said colloidal particle.

It is understood by the skilled person that the dosage of the medicament of the invention is depending on the concentration of the effective biopolymeric substances as well as their efficiency.

A dosage up to 2,000 mg/liposomes lipid per kg body weight can be administered to patients wherein the active factors in the liposomes are loaded with an efficiency of higher than 50% based on the total activity used for preparing the loaded liposomes.

Accordingly, in another aspect of the present invention, the volume of the formulation for delivery into a patient may be no more than 2 ml. Suitably, the delivery volume may be 5 µl, 10 µl, 25 µl, 50 µl, 100 µl, 250 µl, 500 µl, 750 µl, or 1 ml. In alternative embodiments the volume of the formulation for delivery may be no more than 1.5 ml, 2 ml, 2.5 ml, 3.0 ml or 3.5 ml.

It is important to note that the present invention allows for a higher concentration of an active agent to be delivered in a single subcutaneous injection more safely than by intravenous injection, since it is not delivered directly into the bloodstream of the patient. This is particularly important when dealing with blood clotting factors, since high concentration of blood clotting factors administered intravenously can result in undesirable and dangerous blood clots in the patient.

Subcutaneous delivery allows the steady infusion of the active agent into the blood stream via the lymphatic system, thus avoiding the effect of dangerous levels of an active agent being delivered directly into the blood system. Therefore, since the concentration of delivery of the agent into the blood stream is regulated by the lymph system of the patient, a higher concentration may be delivered in a subcutaneous administration dose, which allows for smaller volumes to be used than traditionally used with intravenous delivery.

The formulations of the invention may be for administration at least once per day, at least twice per day, about once per week, about twice per week, about once per two weeks, or about once per month.

For certain therapeutic substances, a dosage regime of once per day will be sufficient, but for others a more frequent dosage regime may be more appropriate or desirable, where the amount delivered in each dosage administered subcutaneously may be reduced relative to a standard intravenous dosage. So for example a formulation of the invention may be administered once per day, twice per day (or more if required).

The present invention allows the prevention of the rapid rise and subsequent fall (i.e. a "sawtooth") in the concentration of a therapeutic agent in the blood. The present invention provides a more consistent, predictable concentration of the agent in the blood of a patient over a longer period of time than is traditionally seen with standard pharmaceutical formulations of the same agent when repeatedly delivered intravenously.

A further benefit of the present invention is that it enables a higher dose of the agent to be administered subcutaneously than may be safely administered intravenously. This results in the provision of a longer duration of the therapeutic benefit than could ordinarily and safely be achieved by higher dosing or more frequent dosing via intravenous delivery. For example, in the case of blood factors, because the products are being delivered via the thoracic duct into the subclavian vein, the method enables a larger amount of product to be administered at a single time point as a single dose subcutaneously than could be administered at a single time point intravenously into a vein. Delivery of a high dose bolus into a vein may cause an undesirable thrombotic event.

A further benefit of the present invention is that it enables the therapeutic agent to be re-dosed at intervals to allow blood concentration of the agent to be maintained at a consistent level, providing a sustained constant and predictable therapeutic effect without the need to wait to re-dose until the concentration of the agent in the blood falls to therapeutically irrelevant levels. In traditional practice, intravenous re-dosing of blood clotting factors, with its immediate $C_{max}$ and onset of action, is delayed until it has been estimated that the level of the therapeutic has dropped to a level at which the addition of the $C_{max}$ from the new injection will not reach a potentially thrombogenic level (i.e. reducing the risk of an adverse event), but which means that the patient has reached an "unhealthy" range of a level of an agent in his or her bloodstream. In other words, subsequent doses of an agent are not normally given to the patient while "healthy levels", or therapeutically effective levels, of the agent are still present in the bloodstream. However, the present invention enables re-dosing of the agent to occur while blood levels of the agent are still in a therapeutic effective range. Thus the invention provides for a more consistent therapeutic level of protein in the bloodstream that is more ideally suited to prophylaxis. Due to the consistent delivery of the agent into the bloodstream via the thoracic duct, the problem of increasing the agent in the bloodstream to undesirably high levels is avoided.

The invention provides a formulation for subcutaneous administration to a subject which enables the subject to receive a dosage form of a blood clotting factor sufficient, to maintain a whole blood clotting time in said subject of no more than 20 minutes, in other words for administration of no more than once per month. Also provided is a formulation of blood coagulation factor for subcutaneous administration no more than once per month wherein the dosage form has a $C_{max}$ of at least 10% and no more than 90% compared to an equivalent reference dosage form when administered intravenously, for use in the treatment of a blood clotting disorder. Suitably, the $C_{max}$ is from 20% to 80%, or from 30% to 70%, or from 40% to 60%.

By "no more than" it is meant that the dosage form may be administered more frequently than the time period specified, but it is not necessary to do so; the effect of the subcutaneous administration of such a dosage form means that the effects are seen for the duration of the time period. However, due to the lower and consistent $C_{max}$, more frequent dosing may occur without adverse effects to the patient.

Suitably, the dosage form of a blood clotting factor may be sufficient to maintain a whole blood clotting time in said subject of less than 15 minutes, or suitably, less than 12 minutes. In an embodiment, the dosage form of a blood clotting factor is an at least once per week dosage form, or at least once per month, at least once per two weeks, at least once per half week dosage form.

Also provided is a dosage formulation according to the invention, in which the dosage of the blood clotting factor is of from 1 to 1000 IU/kg, or from 5 to 500 IU/kg, or from 100 to 250 IU/kg, or from 25 to 50 IU/kg, or from 5 to 50 IU/kg.

The dosage form of the present invention comprising a blood clotting factor allows for a less frequent dosing of the dosage form, which is still sufficient to maintain the whole blood clotting time in a subject of no more than 20 minutes, or no more than 15 minutes, or no more than 10 minutes. In one embodiment, the dosage form is sufficient to maintain whole blood clotting time of less than 12 minutes. The dosage form may provide a no more than once a fortnight, no more than once a week, no more than twice a week, no more than once every three days, no more than once every 2 days, no more than once a day or a more or less frequent dosage form.

It is important to note that one benefit of the present invention is that the dosage form when the agent is a blood clotting factor, does not need to be administered to the patient more frequently than these intervals in order to continue to maintain whole blood clotting time in a healthy range, but it may be administered more frequently in order to help to provide a "steady state" similar to that of a controlled release formulation. A "normal" whole blood clotting time is generally considered by one skilled in the art to be 10 to 12 minutes, and anything under 15 minutes is considered to be healthy in a non-haemophiliac human. Once whole blood clotting time is over 20 minutes, it is considered to be in an unhealthy range. Between 15 and 20 minutes is considered to indicate that although bleeding is under control, it is not normal.

In another embodiment the dosage form is administered less frequently than would be predicted by the plasma half-life of a bolus intravenous injection. For example, a bolus injection of modified Factor IX may be required once a week, whereas the same agent delivered subcutaneously in accordance with the invention, may only be required once per ten days, or less.

According to a further aspect of the invention, there is provided a dosage form of a pharmaceutical composition of 25 to 50 IU/kg of a blood coagulation factor for subcutaneous administration at the same or with less frequency than the blood coagulation factor administered intravenously.

Formulations of the present invention are therefore able to maintain a normal value for haemostasis of up to seven days in which a normal value is defined as a Whole Blood Clotting Time (WBCT) of less than 15 minutes, suitably, about 12 minutes or less.

The formulations of specific embodiments of the invention wherein the formulation comprises a blood factor may comprise a dosage of from 25 to 50 IU/kg. In some embodiments the dosage may be 25, 30, 35, 40, 45, or 50 IU/kg. The dosage may be from 25 IU/kg to 30 IU/kg, 35 IU/kg to 40 IU/kg, or 40 IU/kg to 50 IU/kg.

The formulations of specific embodiments of the invention wherein the formulation comprises a blood factor may alternatively comprise a dosage of from 5 to 50 IU/kg. In some embodiments the dosage may be 5, 10, 15, 20, 25, 30, 35, 40, 45, or 50 IU/kg. The dosage may be from 5 IU/kg to 10 IU/kg, 25 IU/kg to 30 IU/kg, 35 IU/kg to 40 IU/kg, or 40 IU/kg to 50 IU/kg.

In one embodiment, when the dosage form is prepared as a dose of 150 IU/kg, the formulation may be suitable for administration once every two weeks to a subject in need thereof. Suitably, the formulation may be for administration no more than once every two weeks. Alternatively, the dosage may be prepared as a dose of 100 IU/kg.

According to an embodiment of the invention, a formulation of the invention comprising a blood clotting factor can result in normal haemostasis being maintained for at least one half of a week.

Dosage forms in accordance with the invention, when administered subcutaneously result in lower amounts of the modified blood coagulation (clotting) factor being required to achieve the same therapeutic end-point thus providing safer products for subjects in need of treatment. In one embodiment half the adjusted dose of modified blood clotting factor administered intravenously is sufficient to achieve normal haemostasis for at least one week in subjects, particularly wherein the blood coagulation factor is Factor VIIa or Factor VIII. A suitable value for normal haemostasis is a Whole Blood Clotting Time (WBCT) of about 12 minutes, as described above.

Formulations of the invention may suitably comprise less than half the dose adjusted therapeutically effective amount of a reference formulation formulated for intravenous administration comprising the same modified blood coagulation factor in order to achieve the same therapeutic effect.

The invention therefore also provides for a dosage form of a modified blood coagulation factor for subcutaneous administration in which the dosage form comprises 50% of the dose adjusted amount required for intravenous administration in order to achieve the same duration of effective action.

A formulation suitable for subcutaneous administration may suitably be prepared as an aqueous or substantially aqueous formulation. The formulation may comprise such additional salts, preservatives and stabilisers and/or excipients or adjuvants as required. The dosage forms of the invention may be provided as anhydrous powders ready for extemporaneous formulation in a suitable aqueous medium.

Suitably such dosage forms can be formulated as buffered aqueous formulations. Suitable buffer solutions may include, but are not limited to amino acids (for example histidine), salts of inorganic acids and alkali metals or alkaline earth metals, (for example sodium salts, magnesium salts, potassium salts, lithium salts or calcium salts—exemplified as sodium chloride, sodium phosphate or sodium citrate). Other components such as detergents or emulsifiers (for example, Tween 80® or any other form of Tween®) may be present and stabilisers (for example benzamidine or a benzamidine derivative). Excipients such as sugars, (for example sucrose) may also be present. Suitable values for pH are physiological pH, e.g. pH 6.8 to 7.4 or pH 7.0. Liquid dosage forms may be prepared ready for use in such administration vehicles.

In one particular embodiment of the invention, there is provided a pharmaceutical composition for subcutaneous administration as follows:

50 mM sodium citrate pH 7.0

100 mM phospholipids—97:3 molar ratio of palmitoyl-oleoyl phosphatidyl choline (POPC) and 1,2-distearoyl-sn-glycero-3phosphoethanol-amine-N-[poly-(ethyleneglycol)-2000] (DSPE-PEG 2000).

Lyophilised rFVIII (Helixate NexGen)

The invention will now be further described by way of reference to the following examples which are present for the purposes of illustration only and are not be taken as limitations to the invention.

EXAMPLE 1

Synthesis of Liposomes

Mixed lipids were prepared from palmitoyl-oleoyl phosphatidyl choline (POPC) and 1,2-distearoyl-sn-glycero-3-phosphoethanol-amine-N-[poly-(ethyleneglycol)-2000] derivatized with PEG-2000 (PEG with molecular weight 2000 Daltons) (DSPE-PEG 2000), as follows:

Molecular weight of POPC: 760.08 g/mol

Molecular weight of DSPE-2kPEG: 2789.5 g/mol

The final preparation had a concentration of 100 mM phospholipids. A 15% w/v mixture of lipids was made with a 97:3 molar ratio of POPC:DSPE-2kPEG. The following were weighed and mixed:

2.04 g POPC 0.232 g DSPE-2kPEG 14.9 mL tert-butanol (melted in a 35° C. water bath), all placed in a 100 mL Schott bottle.

The mixture was maintained at 35° C. in a water bath and stirred intermittently until all solids had dissolved/dispersed. The final material was a clear colourless mixture. The mixture was frozen at −80° C. overnight.

The operation was maintained in a fume hood to allow containment during the post-use clean-up of dried/condensed solvent. The Christ Alpha 1-2 LD freeze-drier and vacuum pump were warmed up for 20 minutes, and the frozen lipid/solvent mixture was removed from −80° C. storage and dried overnight.

The dried lipids were recovered from the drier the following morning. They appeared as a dry crystalline cake. A 100 mM lipid solution was required for further processing. The quantities of lipid present calculate through as around 82 μmoles of DSPE-2kPEG and 2.69 mmoles of POPC; so around 2.77 mmoles of lipids. Thus 27.7 mL of diluent was required. 27.7 mL of 50 mM sodium citrate buffer was added to the dried lipids, and the resulting mixture was stirred and heated to around 35° C. After around 120 minutes, a white emulsion with no obvious large solids resulted. This was subjected to extrusion as below.

A Sartorius 47 mm stainless steel pressure filtration housing was assembled and wrapped with a water jacket (wrapped tubing fed via a thermocirculator) maintained at 35° C. The housing was fitted with a polycarbonate track-etched membrane (details below), covered by a glass-fibre prefilter (Whatman GF/D). The emulsion was poured into the housing and extruded under 4 bar nitrogen gas, with the filtrate collected into 50 mL tubes. The duration of each extrusion was timed and noted.

The filtration sequence was: 0.8 μm, 0.4 μm, 0.2 μm, 0.2 μm, 0.1 μm and 0.1 μm (i.e. single passes through the larger filters and two passes through the smaller 0.2 and 0.1 μm filters), with the filtrate warmed back to 35° C. between passes. The liposomes were extruded, with tabulated data is below:

TABLE 1

| Pore size (μm) | Duration | Recovery (g) |
|---|---|---|
| 0.8 | <4 sec | 28.19 |
| 0.4 | <4 sec | 26.91 |
| 0.2 | 50 sec | 23.76 |
| 0.2 | 22 sec | 21.77 |
| 0.1 | 12 minutes | 20.18 |
| 0.1 | 4 minutes | 19.47 |

The resulting extruded lipids were stored at +5° C. 15 mL of 'Extruded Liposomes' were removed from the chilled stock and dispensed into a sterile 50 mL tube within a MicroBiological Safety Cabinet. The size of the extruded liposomes was analysed using an ALV5000 photon correlation spectrometer. The average radius was determined to be 75.40±0.86 nm and the average peak width 22.21±3.86 nm, giving an average diameter of 150.80 nm and polydispersity index of 0.087.

EXAMPLE 2

Pharmacokinetics/Pharmacodynamics of Recombinant Human FVIII Reconstituted with PEGylated Liposomes in Haemophilia A Dogs Following Subcutaneous Administration A dog with haemophilia A (identified as dog number "1") received subcutaneous doses of PEGylated liposomes associated with Factor VIII (PEGLip FVIII SQ), as follows:

The objectives of this study were to determine the PK and PD in a haemophilia A dog of full-length rFVIII reconstituted in PEGylated liposomes administered subcutaneously (SQ).

Full-Length rFVIII

Lyophilised, full-length rFVIII (Helixate NexGen, Lot 270LR8WB) was used as the test article.

PEGylated Liposome Formulation

PEGylated Liposomes in citrate buffer were produced in accordance with Example 1 above according to the method of Baru et al. (2005). The Liposome formulation had the following composition; 50 mM sodium citrate pH 7.0 containing 100 mM phospholipids; comprising a 97:3 molar ratio mixture of palmitoyl-oleoylphosphatidylcholine (POPC) and 1,2-distearoyl-sn-glycero-3-phosphoethanol-amine-N-[poly-(ethyleneglycol)-2000] (DSPE-PEG 2000).

The experimental test subject dog was from the haemophilia A colony housed at the University of Alabama Medical School. All dogs have congenital severe haemophilia A. The test subject weighed 16.4 kg and was naive to human proteins.

Prior to dosing, the dog was tested to verify normal health status, including complete blood chemistry, serum chemistry profile fibrinogen, fibrinogen derived peptides (FDPs), thrombin time and urinary analysis The design of this study was a single SQ dose feasibility trial in a single individual.

Full-length, recombinant human FVIII (Helixate NexGen, 2,000 IU) was reconstituted with 13.3 ml of PEGylated liposomal diluent. The reconstituted rFVlll was mixed gently at ambient temperature for 5-10 min to allow the protein to adsorb to the liposomes before use. Once reconstituted, the suspension had a FVIII activity of 150 IU/ml.

The test individual was dosed SQ at 100 IU/kg. Calculation of the volume of drug to be administered was carried out according to the following equation:

$$\text{Dose volume (ml)} = (a \times b)/c$$

Where: a is the target dose (100 IU/kg)
b is the weight of the dog (kg)
c is the rFVIII activity (150 IU/ml)

Following dosing, the test animal was observed for clinical signs. Unexpected toxicities were screened for by performing CBC and serum chemistry tests at 48 hr and 5 days post-dose. Fibrinogen, FDPs and the thrombin time (TT) were evaluated to test for increased thrombosis risk.

Blood samples (5 ml) were taken from the dog dosed SQ at the following times points after administration:

Pre-drug administration and at 0.5, 1, 2, 4, 8, 12, 24, 36, 48, 60, 72, 84, 96, 108 and 120 hours post-dose.

Whole blood (non-citrated; 1 ml) was used for the whole blood clotting assay and the activated clotting time assay. The remaining 4ml blood samples were transferred into tubes containing 0.109M tri-sodium citrate anticoagulant (9:1 v/v) on ice.

The activated Partial Thromboplastin Time (aPTT), Activated Clot Time (ACT) and Thromboelastogram (TEG) assays were conducted on the citrated whole blood.

Plasma was prepared by centrifugation of the remaining citrated blood and the resulting plasma samples were stored in aliquots of approximately 100 µl at −80° C.

Assays (i) Non-Citrated Whole Blood: Whole Blood Clotting Assay

Blood samples were divided between 2 vacutubes, (2×0.5 ml) and observed carefully with periodic and judicious levelling of the tube until a clot was determined by interruption of flow in the fully horizontal position. The quality of the clot was observed by holding the tube in the fully inverted position. The whole blood clotting time was recorded as the mean of the total time from sample extraction until visual observation of blood clot for both samples and the quality of the clot in the inverted position was be noted.

(ii) Citrated Whole Blood: Thromboelastogram (TEG) Assay

TEG was performed with re-calcified citrated whole blood using a Hemostasis Analyzer Model 5000 (Haemoscope Corporation) thromboelastograph according to the manufacturers' recommendations. Briefly, 1 ml of citrated whole blood was placed in a commercially available (Tege-Hemostasis System Kaolin, Haemonetics) vial containing kaolin. Mixing was ensured by gentle inversion of the kaolin-containing vials 5 times. Pins and cups were placed in the TEG analyzer in accordance with the standard procedure recommended by the manufacturer. Each standard TEG cup was placed in the 37° C. pre-warmed instrument holder and was filled with 20 µl of calcium chloride (0.2 M). Then, 340 µl of kaolin-activated citrated whole blood was added for a total volume of 360 µl.

(iii) Activated Clotting Time (ACT) and Activated Partial Thromboplastin Time (aPTT)

The ACT and aPTT tests were carried out using a Haemachron Jr coagulation analyzer (International Technidyne Corps.) according to the manufacturer's instructions.

(iv) Plasma: FVIII Activity Assay (Chromogenic)

FVIII plasma activity was determined using the Coatest Assay (Dia Pharma, West Chester, Ohio). Plasma samples were diluted 1:20 to 1:80 with assay diluent and assayed according to the manufacturers instructions. Standard curves were established using normal hemostasis reference plasma (american diagnostica inc, Stamford, Conn.) and the purified PEG-FVIII protein.

(v) Plasma: FVIII ELISA

The concentration of FVIII antigen in plasma samples will be determined by ELISA using the Visulize FVIII antigen kit from Affinity Biologicals (Ancaster, Ontario, Canada) according to the manufacturer's instructions.

(vi) Plasma: Immunogenicity

Bethesda assays were conducted on 1:4, 1:10 and 1:20 dilutions of test plasma into FVIII deficient human plasma. Equal volumes of the diluted test plasma and normal human reference plasma were incubated at 37° C. for 2 hours and the Bethesda titre determined using the aPTT assay and a normal human plasma standard curve as described above.

TABLE 2

| | |
|---|---|
| Dog Number | 1 |
| Dog weight (kg) | 16.4 |
| Dose (IU/kg) | 100 |
| rFVIII batch number | Lot 270LR8WB |
| Volume of PEGLip diluent used (ml) | 13.3 ml |
| Volume administered (ml) | 10.93 |

Results of the study are shown in Table 3.

TABLE 3

| Date (dd/mm/yy) | Time (hh:mm) | Time post-dose (h) | WBCT 1 (min) | WBCT 2 (min) | WBCT average (min) | ACT-LR (sec) | aPTT-cit (sec) | TEG (r:min) | FVIII activity) (IU/ml) | [FVIII] (ELISA) (% normal) | Bethesda assay (U) |
|---|---|---|---|---|---|---|---|---|---|---|---|
| 26 Nov. 2013 | | 0 | 22 | 34 | 28 | 367 | 189.1 | | ND | ND | |
| 3 Apr. 2014 | | 0 | 28 | 28 | 28 | 347 | 300 | 60 | 0 | ND | ND |
| 8 Apr. 2014 | 12:00 pm | 0.50 | 20 | 22 | 21 | 332 | 300 | | | 1 | |
| | 12:30 pm | 1.00 | 10 | 10.5 | 10.25 | 270 | 158.1 | 30.2 | 0.6 | 2.1 | |
| | 1:30 pm | 2.00 | 8.5 | 10 | 9.25 | 193 | 129.8 | 21.9 | 1.4 | 4 | |
| | 3:25 pm | 4.00 | 10 | 12 | 11 | 211 | 126.2 | 15.6 | 1.9 | 4.3 | |
| | 7:35 pm | 8.00 | 7 | 8 | 7.5 | 200 | 99.4 | 21.9 | 1.4 | 5.2 | |
| | 10:45 pm | 11.25 | 9.5 | 10.5 | 10 | 207 | 94.7 | 20.9 | 2.1 | 5.4 | |
| 9 Apr. 2014 | 11:15 am | 23.75 | 12 | 12 | 12 | 213 | 178.4 | 18.1 | | 3.5 | |
| | 5:05 pm | 29.50 | 12 | 15 | 13.5 | 273 | 140.8 | 22.6 | 0.4 | 3.1 | |
| 10 Apr. 2014 | 12:00 pm | 48.00 | 18 | 18 | 18 | 326 | 156.1 | 60 | | 3.1 | |
| 11 Apr. 2014 | 09:40 | 70.16 | 26 | 24 | 25 | 305 | 387.7 | 60 | | 2.4 | ND |

ND = Not Detectable

The invention claimed is:

1. A method for prophylactically treating a patient suffering from haemophilia A, the method comprising:
administering subcutaneously more than one dose of a pharmaceutical composition comprising Factor VIII and a liposome comprising about 0.5 to 20 mole percent of an amphipathic lipid derivatized with a biocompatible hydrophilic polymer, wherein the Factor VIII is not encapsulated in said liposome, wherein the amphipathic lipid is palmitoyl-oleoyl phosphatidyl choline (POPC) and 1,2-distearoyl-sn-glycero-3-phosphoethanol-amine (DSPE) in a ratio (POPC:DSPE) of from 85 to 99:15 to 1, and wherein the repeated subcutaneous administration of the pharmaceutical composition maintains a whole blood clotting time of less than 15 minutes for 1 hour to 29.5 hours after each dose.

2. The method of claim 1 wherein the liposome is substantially neutral and the polymer carries substantially no net charge.

3. The method of claim 1 wherein the liposome has a mean particle diameter of between about 0.03 to about 0.4 microns (µm).

4. The method of claim 3 wherein the liposome has a mean particle diameter of approximately 0.1 microns (µm).

5. The method of claim 1 wherein the ratio of POPC:DSPE is from 90 to 99:10 to 1.

6. The method of claim 5 wherein the ratio of POPC:DSPE is 97:3.

7. The method of claim 1 wherein said biocompatible hydrophilic polymer is selected from the group consisting of polyalkylethers, polylactic acids and polyglycolic acids.

8. The method of claim 7 wherein said biocompatible hydrophilic polymer is polyethylene glycol.

9. The method of claim 8 wherein the polyethylene glycol has a molecular weight of between about 500 to about 5000 Daltons.

10. The method of claim 9 wherein the polyethylene glycol has a molecular weight of approximately 2000 Daltons.

11. The method of claim 8 wherein the derivatized amphipathic lipid is 1,2-distearoyl-sn-glycero-3-phosphoethanol-amine-N-[poly-(ethyleneglycol)].

12. The method of claim 8 wherein the derivatized amphipathic lipid is 1,2-distearoyl-sn-glycero-3-phosphoethanol-amine-N-[poly-(ethyleneglycol)-2000] (DSPE-PEG 2000).

13. The method of claim 1 wherein the composition additionally comprises another therapeutically active compound.

* * * * *

SEQUENCE LISTING

<160> NUMBER OF SEQ ID NOS: 4

<210> SEQ ID NO 1
<211> LENGTH: 1438
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| Ala | Thr | Arg | Arg | Tyr | Tyr | Leu | Gly | Ala | Val | Glu | Leu | Ser | Trp | Asp | Tyr |
| 1 | | | | 5 | | | | | 10 | | | | | 15 | |
| Met | Gln | Ser | Asp | Leu | Gly | Glu | Leu | Pro | Val | Asp | Ala | Arg | Phe | Pro | Pro |
| | | | 20 | | | | | 25 | | | | | 30 | | |
| Arg | Val | Pro | Lys | Ser | Phe | Pro | Phe | Asn | Thr | Ser | Val | Val | Tyr | Lys | Lys |
| | | | 35 | | | | | 40 | | | | | 45 | | |
| Thr | Leu | Phe | Val | Glu | Phe | Thr | Asp | His | Leu | Phe | Asn | Ile | Ala | Lys | Pro |
| | 50 | | | | | 55 | | | | | 60 | | | | |
| Arg | Pro | Pro | Trp | Met | Gly | Leu | Leu | Gly | Pro | Thr | Ile | Gln | Ala | Glu | Val |
| 65 | | | | 70 | | | | | 75 | | | | | 80 | |
| Tyr | Asp | Thr | Val | Val | Ile | Thr | Leu | Lys | Asn | Met | Ala | Ser | His | Pro | Val |
| | | | | 85 | | | | | 90 | | | | | 95 | |
| Ser | Leu | His | Ala | Val | Gly | Val | Ser | Tyr | Trp | Lys | Ala | Ser | Glu | Gly | Ala |
| | | | 100 | | | | | 105 | | | | | 110 | | |
| Glu | Tyr | Asp | Asp | Gln | Thr | Ser | Gln | Arg | Glu | Lys | Glu | Asp | Asp | Lys | Val |
| | | | 115 | | | | | 120 | | | | | 125 | | |
| Phe | Pro | Gly | Gly | Ser | His | Thr | Tyr | Val | Trp | Gln | Val | Leu | Lys | Glu | Asn |
| | | | 130 | | | | | 135 | | | | | 140 | | |
| Gly | Pro | Met | Ala | Ser | Asp | Pro | Leu | Cys | Leu | Thr | Tyr | Ser | Tyr | Leu | Ser |
| 145 | | | | | 150 | | | | | 155 | | | | | 160 |
| His | Val | Asp | Leu | Val | Lys | Asp | Leu | Asn | Ser | Gly | Leu | Ile | Gly | Ala | Leu |
| | | | | 165 | | | | | 170 | | | | | 175 | |
| Leu | Val | Cys | Arg | Glu | Gly | Ser | Leu | Ala | Lys | Glu | Lys | Thr | Gln | Thr | Leu |
| | | | 180 | | | | | 185 | | | | | 190 | | |
| His | Lys | Phe | Ile | Leu | Leu | Phe | Ala | Val | Phe | Asp | Glu | Gly | Lys | Ser | Trp |
| | | | 195 | | | | | 200 | | | | | 205 | | |
| His | Ser | Glu | Thr | Lys | Asn | Ser | Leu | Met | Gln | Asp | Arg | Asp | Ala | Ala | Ser |
| | | | 210 | | | | | 215 | | | | | 220 | | |
| Ala | Arg | Ala | Trp | Pro | Lys | Met | His | Thr | Val | Asn | Gly | Tyr | Val | Asn | Arg |
| 225 | | | | | 230 | | | | | 235 | | | | | 240 |
| Ser | Leu | Pro | Gly | Leu | Ile | Gly | Cys | His | Arg | Lys | Ser | Val | Tyr | Trp | His |
| | | | | 245 | | | | | 250 | | | | | 255 | |
| Val | Ile | Gly | Met | Gly | Thr | Thr | Pro | Glu | Val | His | Ser | Ile | Phe | Leu | Glu |
| | | | 260 | | | | | 265 | | | | | 270 | | |
| Gly | His | Thr | Phe | Leu | Val | Arg | Asn | His | Arg | Gln | Ala | Ser | Leu | Glu | Ile |
| | | | 275 | | | | | 280 | | | | | 285 | | |
| Ser | Pro | Ile | Thr | Phe | Leu | Thr | Ala | Gln | Thr | Leu | Leu | Met | Asp | Leu | Gly |
| | | | 290 | | | | | 295 | | | | | 300 | | |
| Gln | Phe | Leu | Leu | Phe | Cys | His | Ile | Ser | Ser | His | Gln | His | Asp | Gly | Met |
| 305 | | | | | 310 | | | | | 315 | | | | | 320 |
| Glu | Ala | Tyr | Val | Lys | Val | Asp | Ser | Cys | Pro | Glu | Glu | Pro | Gln | Leu | Arg |
| | | | | 325 | | | | | 330 | | | | | 335 | |
| Met | Lys | Asn | Asn | Glu | Glu | Ala | Glu | Asp | Tyr | Asp | Asp | Asp | Leu | Thr | Asp |
| | | | 340 | | | | | 345 | | | | | 350 | | |
| Ser | Glu | Met | Asp | Val | Val | Arg | Phe | Asp | Asp | Asp | Asn | Ser | Pro | Ser | Phe |
| | | | | 355 | | | | | 360 | | | | | 365 | |

-continued

```
Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Val Arg Phe Met Ala Tyr Thr
            420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
                755                 760                 765

Asp Tyr Asp Asp Thr Ile Ser Val Glu Met Lys Lys Glu Asp Phe Asp
770                 775                 780

Ile Tyr Asp Glu Asp Glu Asn Gln Ser Pro Arg Ser Phe Gln Lys Lys
```

-continued

|     |     |     |     |     |     |     |     |     |     |     |     |     |     |     |
|---|---|---|---|---|---|---|---|---|---|---|---|---|---|---|
| 785 | | | | | 790 | | | | | 795 | | | | 800 |

Thr Arg His Tyr Phe Ile Ala Ala Val Glu Arg Leu Trp Asp Tyr Gly
                    805                 810                 815

Met Ser Ser Ser Pro His Val Leu Arg Asn Arg Ala Gln Ser Gly Ser
                    820                 825                 830

Val Pro Gln Phe Lys Lys Val Phe Gln Glu Phe Thr Asp Gly Ser
                    835                 840                 845

Phe Thr Gln Pro Leu Tyr Arg Gly Glu Leu Asn Glu His Leu Gly Leu
                    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                    885                 890                 895

Ser Tyr Glu Glu Asp Gln Arg Gln Gly Ala Glu Pro Arg Lys Asn Phe
                    900                 905                 910

Val Lys Pro Asn Glu Thr Lys Thr Tyr Phe Trp Lys Val Gln His His
                    915                 920                 925

Met Ala Pro Thr Lys Asp Glu Phe Asp Cys Lys Ala Trp Ala Tyr Phe
                    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                    965                 970                 975

Val Thr Val Gln Glu Phe Ala Leu Phe Phe Thr Ile Phe Asp Glu Thr
                    980                 985                 990

Lys Ser Trp Tyr Phe Thr Glu Asn Met Glu Arg Asn Cys Arg Ala Pro
                    995                1000                1005

Cys Asn Ile Gln Met Glu Asp Pro Thr Phe Lys Glu Asn Tyr Arg
                    1010               1015               1020

Phe His Ala Ile Asn Gly Tyr Ile Met Asp Thr Leu Pro Gly Leu
                    1025               1030               1035

Val Met Ala Gln Asp Gln Arg Ile Arg Trp Tyr Leu Leu Ser Met
                    1040               1045               1050

Gly Ser Asn Glu Asn Ile His Ser Ile His Phe Ser Gly His Val
                    1055               1060               1065

Phe Thr Val Arg Lys Lys Glu Glu Tyr Lys Met Ala Leu Tyr Asn
                    1070               1075               1080

Leu Tyr Pro Gly Val Phe Glu Thr Val Glu Met Leu Pro Ser Lys
                    1085               1090               1095

Ala Gly Ile Trp Arg Val Glu Cys Leu Ile Gly Glu His Leu His
                    1100               1105               1110

Ala Gly Met Ser Thr Leu Phe Leu Val Tyr Ser Asn Lys Cys Gln
                    1115               1120               1125

Thr Pro Leu Gly Met Ala Ser Gly His Ile Arg Asp Phe Gln Ile
                    1130               1135               1140

Thr Ala Ser Gly Gln Tyr Gly Gln Trp Ala Pro Lys Leu Ala Arg
                    1145               1150               1155

Leu His Tyr Ser Gly Ser Ile Asn Ala Trp Ser Thr Lys Glu Pro
                    1160               1165               1170

Phe Ser Trp Ile Lys Val Asp Leu Leu Ala Pro Met Ile Ile His
                    1175               1180               1185

Gly Ile Lys Thr Gln Gly Ala Arg Gln Lys Phe Ser Ser Leu Tyr
                    1190               1195               1200

Ile Ser Gln Phe Ile Ile Met Tyr Ser Leu Asp Gly Lys Lys Trp
1205                1210                1215

Gln Thr Tyr Arg Gly Asn Ser Thr Gly Thr Leu Met Val Phe Phe
1220                1225                1230

Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser
1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
1280                1285                1290

Ala Gln Ile Thr Ala Ser Ser Tyr Phe Thr Asn Met Phe Ala Thr
1295                1300                1305

Trp Ser Pro Ser Lys Ala Arg Leu His Leu Gln Gly Arg Ser Asn
1310                1315                1320

Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
1400                1405                1410

Ile His Pro Gln Ser Trp Val His Gln Ile Ala Leu Arg Met Glu
1415                1420                1425

Val Leu Gly Cys Glu Ala Gln Asp Leu Tyr
1430                1435

<210> SEQ ID NO 2
<211> LENGTH: 110
<212> TYPE: PRT
<213> ORGANISM: Homo sapiens

<400> SEQUENCE: 2

Ser Tyr Ser Asp Gly Asp Gln Cys Ala Ser Ser Pro Cys Gln Asn
1               5                   10                  15

Gly Ser Cys Lys Asp Gln Leu Gln Ser Tyr Ile Cys Phe Cys Leu Pro
                20                  25                  30

Ala Phe Glu Gly Arg Asn Cys Glu Thr His Lys Asp Asp Gln Leu Ile
        35                  40                  45

Cys Val Asn Glu Asn Gly Gly Cys Glu Gln Tyr Cys Ser Asp His Thr
        50                  55                  60

Gly Thr Lys Arg Ser Cys Arg Cys His Glu Gly Tyr Ser Leu Leu Ala
65                  70                  75                  80

Asp Gly Val Ser Cys Thr Pro Thr Val Glu Tyr Pro Cys Gly Lys Ile
                85                  90                  95

Pro Ile Leu Glu Lys Arg Asn Ala Ser Lys Pro Gln Gly Arg
                100                 105                 110

```
<210> SEQ ID NO 3
<211> LENGTH: 17
<212> TYPE: PRT
<213> ORGANISM: Homo sapiens

<400> SEQUENCE: 3

Lys Pro Val Ala Phe Ser Asp Tyr Ile His Pro Val Cys Leu Pro Asp
1               5                   10                  15

Arg

<210> SEQ ID NO 4
<211> LENGTH: 110
<212> TYPE: PRT
<213> ORGANISM: Homo sapiens

<400> SEQUENCE: 4

Gly His Gln Phe Glu Gly Ala Glu Glu Tyr Ala Ser Phe Leu Gln Glu
1               5                   10                  15

Ala Gln Val Pro Phe Leu Ser Leu Glu Arg Cys Ser Ala Pro Asp Val
            20                  25                  30

His Gly Ser Ser Ile Leu Pro Gly Met Leu Cys Ala Gly Phe Leu Glu
        35                  40                  45

Gly Gly Thr Asp Ala Cys Gln Gly Asp Ser Gly Gly Pro Leu Val Cys
    50                  55                  60

Glu Asp Gln Ala Ala Glu Arg Arg Leu Thr Leu Gln Gly Ile Ile Ser
65                  70                  75                  80

Trp Gly Ser Gly Cys Gly Asp Arg Asn Lys Pro Gly Val Tyr Thr Asp
                85                  90                  95

Val Ala Tyr Tyr Leu Ala Trp Ile Arg Glu His Thr Val Ser
            100                 105                 110
```